(12) United States Patent
Shoji et al.

(10) Patent No.: US 7,081,191 B2
(45) Date of Patent: Jul. 25, 2006

(54) CAPILLARY ELECTROPHORESIS DEVICE

(75) Inventors: Tomihiro Shoji, Hitachinaka (JP); Masaya Kojima, Mito (JP); Yoshiyuki Okishima, Minori (JP); Ryoji Inaba, Hitachinaka (JP)

(73) Assignee: Hitachi High-Technologies Corporation (JP)

( * ) Notice: Subject to any disclaimer, the term of this patent is extended or adjusted under 35 U.S.C. 154(b) by 446 days.

(21) Appl. No.: 10/239,308

(22) PCT Filed: Jan. 18, 2002

(86) PCT No.: PCT/JP02/00345

§ 371 (c)(1), (2), (4) Date: Sep. 20, 2002

(87) PCT Pub. No.: WO03/062814

PCT Pub. Date: Jul. 31, 2003

(65) Prior Publication Data

US 2004/0003994 A1    Jan. 8, 2004

(51) Int. Cl.
*G01N 27/447* (2006.01)
*G01N 27/953* (2006.01)

(52) U.S. Cl. ............... 204/455; 204/453; 204/604; 204/605

(58) Field of Classification Search ............... 204/451, 204/453, 454, 455, 601, 604, 605
See application file for complete search history.

(56) References Cited

U.S. PATENT DOCUMENTS

| 5,635,050 A * | 6/1997 | Pentoney et al. ........... 204/605 |
| 6,375,819 B1 * | 4/2002 | Li et al. .................... 204/455 |
| 6,383,356 B1 * | 5/2002 | Hayashizaki et al. ....... 204/605 |
| 2001/0017263 A1 * | 8/2001 | Shoji et al. ................ 204/455 |

FOREIGN PATENT DOCUMENTS

| JP | 2001-242140 | 9/2001 |
| JP | 2001-281221 | 10/2001 |
| JP | 2001-324473 | 11/2001 |

* cited by examiner

*Primary Examiner*—Kaj K. Olsen
(74) *Attorney, Agent, or Firm*—Dickstein Shapiro Morin & Oshinsky

(57) ABSTRACT

The capillary electrophoresis device using one pressure-resistant syringe (125) is capable of automatically suctioning in polymer solution and injecting polymer solution into a capillary array (100). An electric hook (131) is installed for pulling up the syringe plunger on a push-in action type syringe (125). A check valve (124) is inserted between a polymer bottle (123) and syringe to prevent solution from flowing back into the polymer bottle. As a result, one syringe portion of polymer solution can be suctioned and injected, a large volume of polymer solution can be continuously used and device processing capability is improved.

12 Claims, 8 Drawing Sheets

CAPILLARY ELECTROPHORESIS DEVICE

This application is a 371 of PCT/JP02/00345, filed on Jan. 18, 2002.

TECHNICAL FIELD

The present invention relates to a capillary electrophoresis device and relates in particular to a capillary electrophoresis device having a mechanism for filling a sample separator medium of polymer solution into a capillary.

BACKGROUND ART

Electrophoresis devices utilizing a gel as the flow medium to fill into a capillary have been developed containing a gel filling mechanism for replacing the gel in the capillary so that a large number of samples can be continuously and efficiently analyzed.

For example, a Prism 310 device made by Applied Biosystems (Corp.), injects polymer solution into (one) capillary using a glass syringe. However, since there is no fill mechanism, the amount of polymer solution that can continuously be used is determined by the volume of the syringe. The 3100 unit made by Applied Biosystems (Corp.), that fills polymer solution from a polymer fill syringe to a polymer injection syringe, has a polymer injection syringe (volume of 250 micro-liters) for injecting polymer solution into a capillary array comprised of 16 capillaries and also has a 5 milliliter glass syringe for filling the polymer solution. The fill syringe however is pressurized and sends polymer solution to the injection syringe by utilizing a dedicated drive system.

Devices for filling a viscous polymer solution into a capillary having a diameter from several dozen to several hundred micrometers require a high pressure of approximately several megapascals for performing the filling operation within a short time. Device must also be able to store a large volume of polymer solution in order to continuously process many samples.

In the above Prism 310, the amount of polymer that can be continuously utilized is limited by the syringe volume. Generally, high pressure syringes capable of withstanding a pressure of several megapascals or more have a small volume so this method is not suitable for processing large quantities of polymer solution. Also, when the fill syringe can hold a large amount of polymer solution, a greater force must be applied to press in the fill syringe. Finding a syringe having both the required volume and pressure-resistance is difficult and even if a suitable syringe could be prepared, a large load would be applied to the drive system.

The present invention therefore has the object of providing a capillary electrophoresis device capable of a raising the throughput when continuously using and analyzing large quantities of polymer solution.

DISCLOSURE OF THE INVENTION

The capillary electrophoresis device of the present invention is capable of continuously using large quantities of polymer to raise device processing performance by storing a large quantity of polymer solution in a large capacity polymer storage container, automatically drawing in polymer solution from the polymer storage container using one syringe and injecting the polymer solution into the capillary. The drawing in (suctioning in) of polymer solution from the polymer storage container and into the syringe and then injecting the polymer solution into capillary array is performed by a flow path block formed with a flow path in the interior. The flow path within the flow path block is formed to allow contaminated air in the flow path to be easily exhausted (bled away) when installing or detaching the capillary array. The flow path is also formed to be narrow near the capillary array to reduce the volume of the flow path overall and minimize the consumption the polymer solution and also formed to have a flowing shape to minimize stagnation.

In other words, A capillary electrophoresis device comprising: a capillary array; a polymer storage container for holding polymer solution; a pressure-resistant syringe for pressurizing said polymer solution in said capillary array; a buffer container for holding buffer solution; a flow path block, to which a tip of said capillary array and said pressure-resistant syringe are connected, formed with flow paths for joining at least said tip of the capillary array, said polymer storage container, said pressure-resistant syringe, and said buffer container; a check valve for allowing a fluid medium to flow towards said flow path block from said polymer storage container side and preventing said fluid medium from flowing from said flow path block towards said polymer storage container side; and a plunger drover for driving said pressure-resistant syringe plunger in the push-in direction and pull-out direction; and further characterized by drawing polymer solution into said pressure-resistant syringe from said polymer storage container by way of said flow path block, and injecting said polymer solution drawn from said pressure-resistant syringe into said capillary array by way of said flow path block.

The polymer storage container may be a container open to the atmosphere or an airtight container which has a syringe structure. When using an open type container as the polymer storage container, the polymer storage container should preferably be positioned so that the surface (level) of the polymer solution within the polymer storage container is always lower than the surface of the solution within the buffer container. Alternatively, when at least the polymer storage container and buffer container are joined by the flow path, and also when exposed to an atmospheric air pressure, the polymer storage container is preferably positioned so that the level of polymer fluid within the polymer storage container is lower than the level of solution within the buffer container.

The plunger drive means may be comprised of a stepping motor, a direct-driven actuator for converting the rotation of the stepping motor into linear movement, a moving piece for applying contact pressure to the rear edge of the plunger fixed to the direct-driven actuator, and a linear encoder to output a signal showing the position of the moving piece. The moving piece may also contain an inward/outward moving hook, and the plunger is clamped by the hook when the plunger is driven in the extraction (pull-out) direction.

Preferably, a plurality of speeds may be set as the plunger pull-out speed when suctioning (drawing in) the polymer solution to the syringe from the polymer storage container and the plunger pull-out speed can be selected according to the viscosity of the polymer solution.

The flow path block has a side hole, to which the tip of the capillary array is inserted. Inside the side hole, the upper edge of the end wall has an opening for a flow path connecting the pressure-resistant syringe and polymer storage container. An opening for a flow path connecting to the buffer container is located in the lengthwise direction of that side hole, on the bottom side at approximately the mid-point.

A capillary electrophoresis device of the present invention comprising: one or more capillaries capable of being filled with a separator medium for separating a sample; a first buffer container for holding a first buffer solution for immersing a portion of said one or more capillaries; a second buffer container for holding a second buffer solution; polymer container for holding said separator medium; a pressure-resistant syringe capable of drawing in and pushing out said separator medium; a plunger shift mechanism having a press-force section to press the plunger of said pressure-resistant syringe, and a pull-in section to pull said plunger; said pull-in section being capable of changing from a state pulling the plunger to a state not pulling the plunger; a first flow path joining said one or more capillaries and said second buffer container; a second flow path joining said polymer container and said pressure-resistant syringe; a third flow path joining said pressure-resistant syringe and said one or more capillaries; and a check valve installed in said second flow path, allowing said separator medium to flow from said polymer container towards said pressure-resistant syringe, and for preventing said separator medium from flowing towards said polymer container from said pressure-resistant syringe.

The plunger shift mechanism in the electrophoresis device is placed at the specified position by turning on the power to the electrophoresis device and/or by instructions to operate the pressure-resistant syringe, or is shifted to the pull-in direction.

A method of the present invention for injecting a separator medium into one or more capillaries by a pressure-resistant syringe capable of drawing in said separator medium and injecting said separator medium into said one or more capillaries and a shift mechanism capable of moving a plunger of said pressure-resistant syringe, comprising following steps being performed prior to injecting said separator medium into said one or more capillaries:

(1) placing said shift mechanism in a specified position;

(2) moving said shift mechanism to make contact with said plunger; and (3) determining amount of said separator medium in said pressure-resistant syringe based on amount of movement of said shift mechanism from the specified position until making contact with said plunger.

Preferably a following step (4) is performed prior to injecting the separator medium into the one or more capillaries.

(4) moving the shift mechanism to drive the plunger, and draw in (suction in) separator medium into the pressure-resistant syringe, when the separator medium within the pressure-resistant syringe is below a specified amount.

Preferably a following step (5) is also performed.

(5) moving the shift mechanism to drive the plunger, and inject the separator medium into the one or more capillaries when the separator medium within the pressure-resistant syringe is a specified amount or more.

The shift mechanism may have a pull-in section capable of pulling up the plunger, and the step (4) may include a procedure for the shift mechanism to position the pull-in section capable of pulling up the plunger, to a plunger pull-up position. Alternatively, the step (4) may include a procedure for driving the plunger at a movement speed based on the type of separator medium, and draw the separator medium into the pressure-resistant syringe.

BEST MODE FOR CARRYING OUT THE INVENTION

The present invention is next related in detail while referring to the accompanying work drawings.

Figure 1:
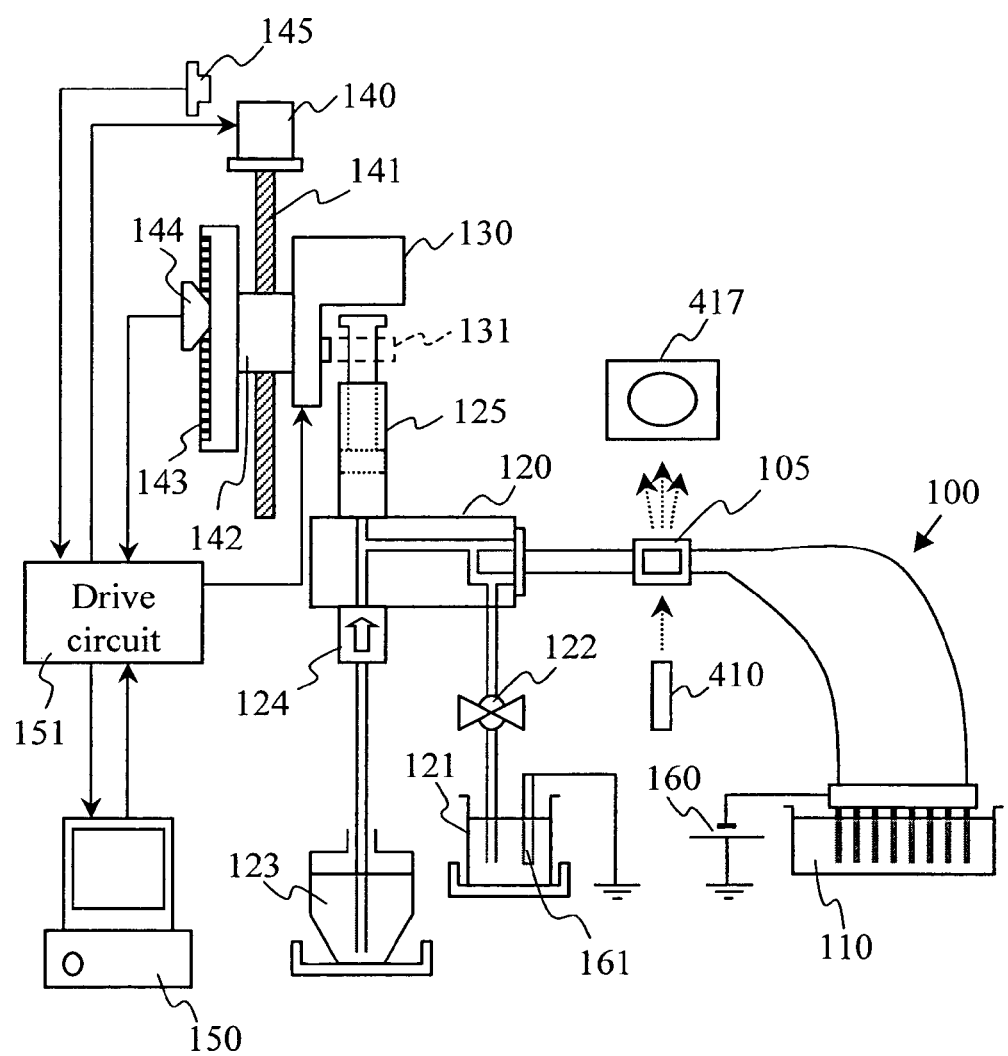
FIG. 1 is an overall structural view showing an example of the capillary electrophoresis device of the present invention.

FIG. 1 is an overall structural view showing an example of the capillary electrophoresis device of the present invention.

The capillary electrophoresis device has a capillary electrophoresis section and optical sensor section, along with a polymer injection mechanism for injecting the electrophoresis separator medium consisting of high viscosity polymer into the capillary (fine tube with inner diameter from several dozen to several hundred micrometers). The polymer injection mechanism draws in (suctions in) the polymer solution from a polymer bottle 123 by operating one glass syringe 125 having a pressure resistance of several to several dozen [MPa] megapascals, and injects that polymer solution into capillary array consisting of, for example, 96 elements in an automatic operation.

An overview of the device structure is described next. One end (sample injection end) of the capillary array unit consisting of 96 elements is immersed in a buffer inside a buffer container 110. The other end (of the capillary array unit 100) is connected to the flow path block 120. Besides the capillary array unit 100, a glass syringe 135 and a polymer bottle 123 containing polymer solution for injection into the capillary 121, are connected to the flow path block 120, and the interior is formed with flow paths connecting to these parts (100 and 123). The flow paths within the flow block are narrow tubes approximately one millimeter in diameter in order to reduce dead volume and eliminate air bubbles. The section connecting the capillary array unit 100 is formed to have a narrow flow path to match the shape of the capillary array, thus enabling ease to eliminate the air bubbles at array replacement. The flow path block 120 is formed of a transparent material such as acrylic to improve the visibility of the internal flow paths.

A check valve 124 is installed between the flow path block 120 and the polymer bottle 123. During injection of polymer solution from the glass syringe 125 to the capillary of the capillary array unit 100, the check valve 124 prevents the polymer solution from flowing back into the polymer bottle 123. However, the flow path preferably offers little resistance to impede the operation of drawing in polymer solution into the glass syringe 125 from the polymer bottle 123. The section between the flow path block 120 and the polymer bottle 123 is not limited to a location physically enclosed by these two parts. In other words, this statement signifies that the check valve 124 is at a position capable of blocking the flow of polymer solution from the glass syringe 125 to the polymer bottle 123.

A polymer bottle 123 having a volume sufficient for continuous operation is utilized, and the bottom is formed in a cone shape so that no air bubbles are mixed in even when there is little remaining polymer solution. The exhaust valve or the tube insertion opening has a gap sufficient to prevent a negative pressure in the bottle even when drawing in polymer solution. The polymer bottle 123 is also installed at a position lower than the buffer container 121 so that the polymer solution does not flow back from the polymer bottle 123 to the buffer container 121 due to a high or low pressure differential. The inflow of polymer solution or buffer fluid into the polymer bottle 123 is prevented at this time by the operation of the check valve 124.

The polymer bottle 123 installation position may be changed to a position higher than the buffer container 121, when not allowing polymer solution to flow back from the polymer bottle 123 to the buffer container 121 side, just (the same) as when the buffer valve 122 was closed to inject polymer solution into the capillary of the capillary array unit 100. In other words, the polymer bottle 123 must be installed at a position lower than the buffer container 121, when forming at least the flow path joining the polymer bottle 123 and the buffer container 121.

An electric buffer valve 122 is installed between the buffer container 121 and the flow path block 120. The buffer valve 122 is closed when injecting polymer solution into the capillary of the capillary array unit 100, and closing the flow path between the capillary array and the buffer container. The buffer valve 122 is opened during electrophoresis, opening the flow path and connecting the capillary array and buffer container.

Figure 2:
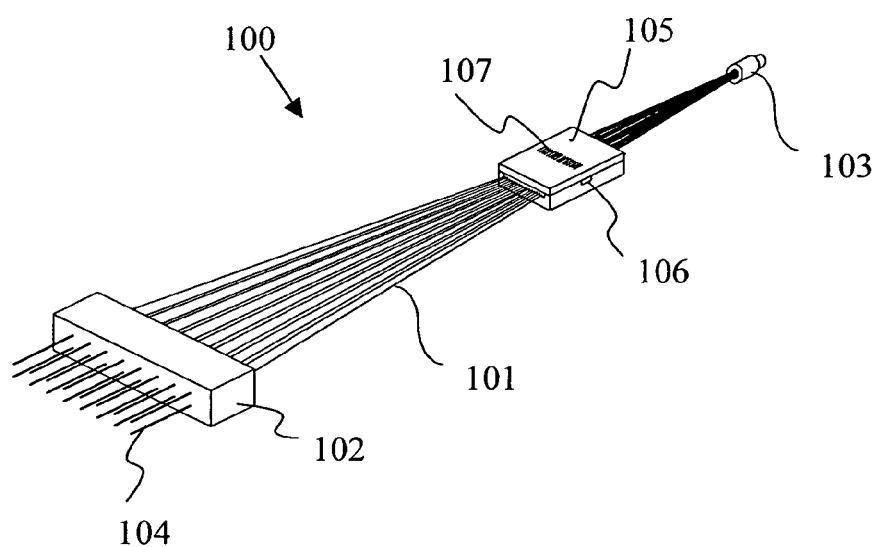
FIG. 2 is a drawing showing an example of the capillary array unit.

FIG. 2 is a drawing showing the capillary array unit 100. Each capillary piece 101 comprising the capillary array 100 has an outside diameter 0.1 to 0.7 millimeters and an inner diameter of 0.02 to 0.5 millimeters, and an outer coating of polyimide resin. The capillary itself is comprised of multiple (in this example 96 pieces) quartz pipes (or tubes) arranged to form a capillary array. The capillary array unit 100 is comprised of a load header 102 to input (fluorescent) dye-marked DNA samples from the sample container into the capillary by electrophoresis, a window unit 105 to array and clamp the capillaries 101 in the sample number sequence of load header 102, and a capillary head 103 having multiple capillaries bundled and adhered together. A hollow electrode 104 for applying the electrophoretic effect to the capillary, is installed in the sample injection end (tip) and protrudes from the load header 102. The window unit 105 contains an opening 106 for beaming light from the side onto the arrayed and supported capillaries and an opening 107 to extract the fluorescent light emitted from the capillaries.

The shape of the capillary head 103 of the capillary array unit, or in other words the shape of the connecting section that connects with the flow path block 120, may be flat shape with the capillaries arrayed in a row or a round shape with the capillaries together in one bundle. In the case of a round shape, the capillary head 103 can be attached to the flow path block 120 by installing a sleeve onto the capillary head 103 and screwing it on by pushing from behind, to deform the sleeve to fill in the gap. The previously described Applied Biosystems (Corp.) Prism 3100 utilizes this method.

Figure 3:
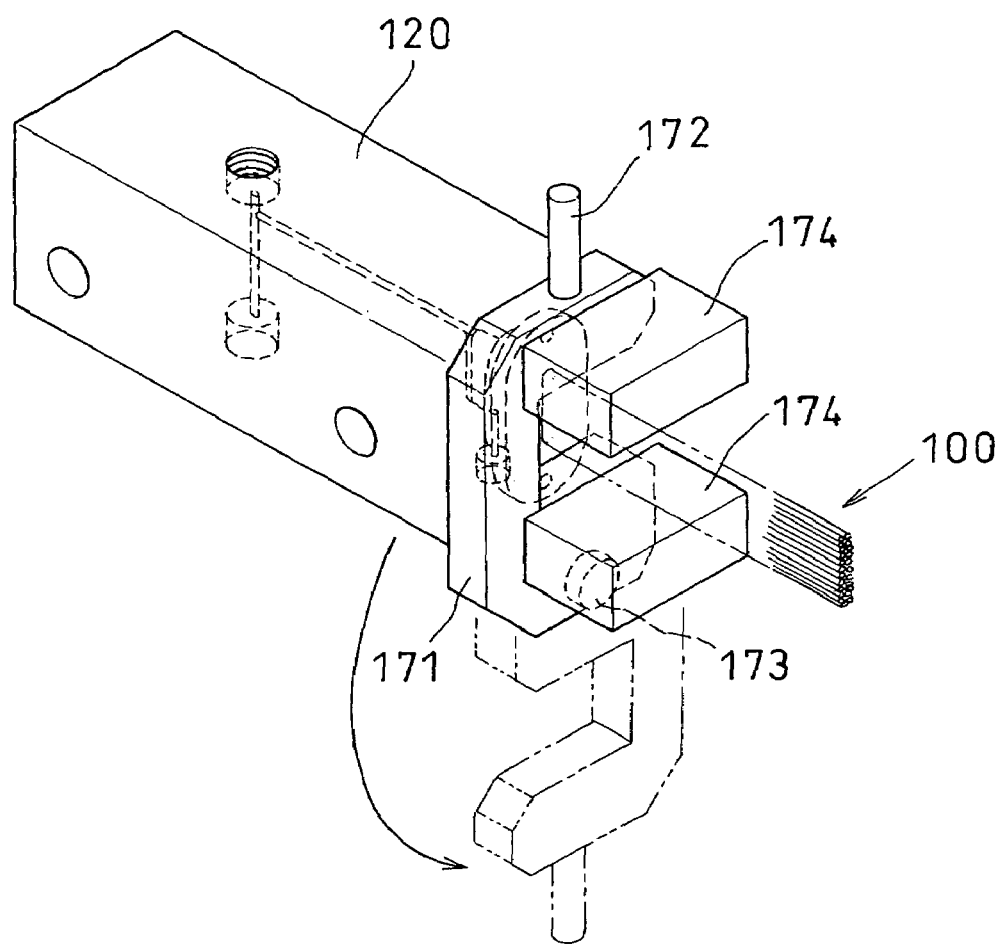
FIG. 3 is a drawing showing the method for clamping the flow path block of the capillary array unit.

FIG. 3 is a drawing showing an example of the method for clamping to the flow path block of the capillary array unit when the connecting section for connecting to the flow path block is a flat shape. In this method, a spacer is inserted between the capillary array unit connecting section and the stopper positioned behind it and the capillary array unit 100 clamped.

Stoppers 174 are clamped to the equipment cabinet at a specified gap on the surface edge where the capillary unit 100 connecting section of flow path block 120 is installed. A spacer 171 capable of movement is installed around the rod 173. When the knob 172 is gripped and turned, the spacer 171 enters between the flow path block 120 and the stopper 174. The edge of the capillary array unit 100 therefore fits into the connecting hole of the flow path block 120, and when the spacer 171 is then rotated from the dashed line position to the solid line position, and the capillary array unit 100 is inserted between the flow path block 120 and the stopper 174, the edge of the spacer 171 on the flow path block side makes contact with the flange installed on the capillary head of capillary array unit 100, and the capillary array unit 100 is clamped to the flow path block 120. The flange of the capillary array unit 100 is sealed to the flow path block 120 by an O-ring.

In the method shown in FIG. 3, the capillary array unit 100 can easily be installed to or removed from the flow path block 120 in a simple operation by just removing or inserting the spacer 171. Besides the method shown in FIG. 3, there is also a method for clamping (100) to the flow path block by pushing an item such as a bolt in from the rear by way of an O-ring, etc.

Figure 4A:
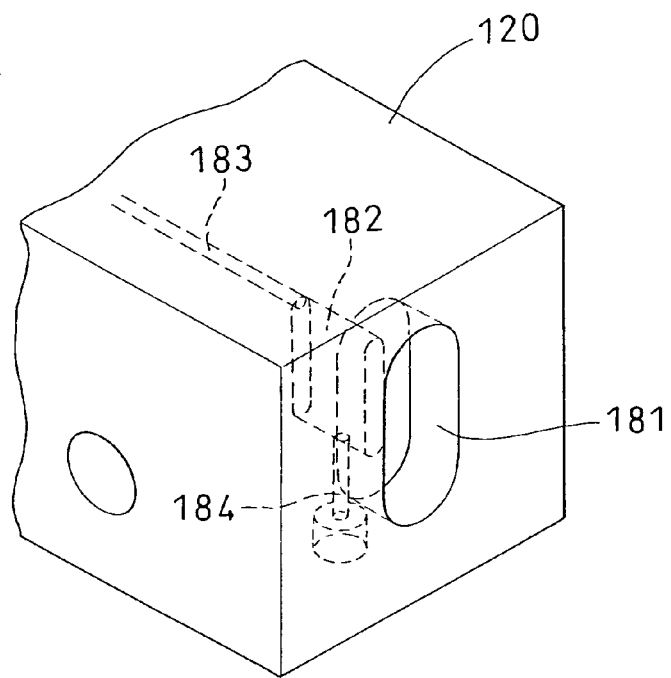
FIGS. 4A, 4B and 4c are drawings showing in detail the capillary array unit connection section for the flow path block.
Figure 4B:
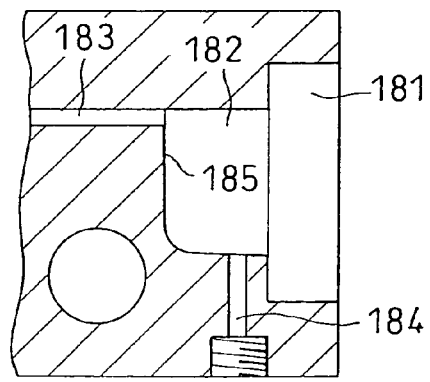
Figure 4C:
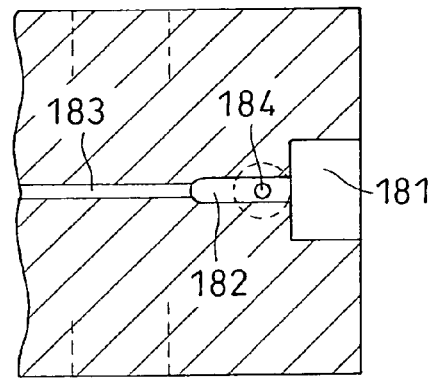

FIG. 4A through 4c are drawings showing in detail the capillary array unit connection section for (attaching to) the flow path block. The flange tip of the capillary of the capillary array unit 100 is inserted into a relatively large diameter side hole 181 formed on one end of the flow path block 120 as shown in FIG. 4A. Inside the side hole 181, the tip of the capillary array protruding from the capillary head is inserted into a relatively small diameter side hole 182. A narrow flow path 183 connecting to the glass syringe 125 and the polymer bottle 123 is formed on the upper side of the wall where the side hole 182 ends. A narrow flow path 184 is formed on the bottom edge at about midpoint as seen along the depth direction of side hole 182 to connect to the buffer container 121 preferably at a position as near as possible to the large diameter side hole 182. The space between the side hole 182 and capillary array tip should be as narrow as possible in a range capable of obtaining electrophoretic movement. This (narrow flow path) reduces the dead volume of the flow path and provides a uniform flow speed distribution to allow easily bleeding away air bubbles. The wall 185 end and its bottom are both curved surfaces as shown in the elevational view in FIG. 4B and top plan view in FIG. 4C. By adopting this kind of structure, even if air penetrates into the flow path during installation or removal of the capillary array from the flow block 120, air bubbles can be evacuated into the buffer container and the polymer solution can flow without accumulating by opening the buffer valve 122 and allowing polymer solution to flow.

Figure 5:
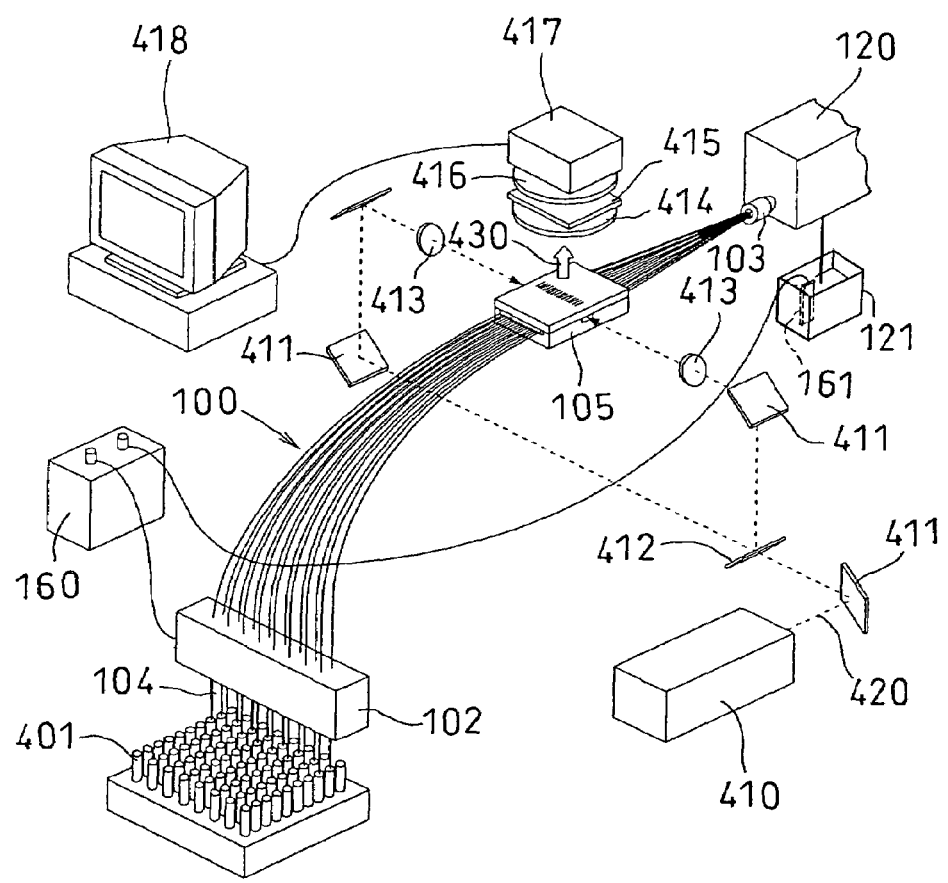
FIG. 5 is drawing showing the optical sensor output section and electrophoresis drive section of the electrophoresis device of the present invention.

FIG. 5 is a drawing showing the optical sensor output section and electrophoresis drive section of the electrophoresis device of the present invention. The flow drive section shown in FIG. 5 is the structure when injecting sample material into the capillary. At one end of the capillary array unit 100 shown in FIG. 2, the hollow electrodes 104 protruding from the load header 102 and sample injection tips of the capillary 101 are immersed in sample tray having a plurality of sample containers 401 holding (fluorescent) dye-marked DNA samples, and the capillary head 103 at the other end (of capillary array unit 100) is attached in an air-tight, pressure resistant connection to the flow path block 120 holding polymer solution. A high voltage of approximately 15 kilovolts from the high voltage power supply 160 is applied to the hollow electrode 104 of the load header 102 and the electrode 161 immersed in the buffer container 121 connected to the flow path block 120, so that the samples in the sample containers 401 are injected into each capillary of the capillary array by an electric field injection method. The sample injection tip of the capillary array unit 100 is then immersed in the buffer container 110 as shown in FIG. 1 and the samples injected by the electric field undergo electrophoresis and are separated.

A laser light source 410 beams an excitation light 420 onto a sensor section (window unit) 105 by utilizing an excitation laser system made up of a mirror 411, a beam splitter 412 and a condensing lens 413, etc. A fluorescent light 430 which is signal light emitted from the material subjected to electrophoresis in the capillary due to beaming of excitation light is detected by a CCD camera 417 by way of a detection lens system made up of a first lens 414, optical filter and image segmenting Prism 415, and a second lens 416. The detected signal is processed in the signal processor device 418.

The optical detection system shown in the figure beams a laser beam from the side surface of the capillary array containing electrophoresized DNA or protein material, beams excitation light onto all the capillaries from laser beam condensed by utilizing the capillary lens, and detects the fluorescent light from each capillary utilizing the optical detection system. The laser (excitation) beam 420 may also have a structure for beaming light only from the side of the capillary array, and the photosensitive (light-sensitive) optical system is not limited to the structure shown in FIG. 5.

Returning to FIG. 1, the polymer injection mechanism of the electrophoresis device of the present invention is described next.

The stepping motor 140 and the direct-driven actuators 141, 142 drive the moving piece 130 that operates the glass syringe 125. When a polymer solution is injected into the capillary of the capillary array unit 100, the motor 140 rotates in the forward direction, lowering the moving piece 130, and making the moving piece 130 press down the plunger on the glass syringe 125. The injection pressure is determined by the speed of the moving piece 130 and the overall flow path resistance including the capillary array. However, when the moving piece 130 speed is overwhelmingly faster than the polymer flow speed, the motor enters a step-out state and the injection pressure reaches its upper limit. The pressure at which the motor enters the step-out state is determined by value of electrical current flowing in the motor. The injection pressure can be controlled within its upper limit by adjusting this electrical current. The injection pressure upper limit is usually set to be lower than the breakdown pressure of the overall system. The glass syringe 125 has the least pressure resistance in the polymer injection mechanism so the pressure is adjusted to be lower than the glass syringe. The moving piece 130 also contains an electrically inward/outward moving hook. When pulling the plunger of the glass syringe 125 upward, the hook 131 is pressed outwards in the forward direction. When the motor 140 is rotated in reverse with the hook 131 sticking out, the screw 141 and the slider 142 engaging with the screw 141 move the moving piece 130 upward and in this way can pull the syringe 125 upward. The motor 140 is controlled by the computer 150 by way of the drive circuit 151.

Figure 6:
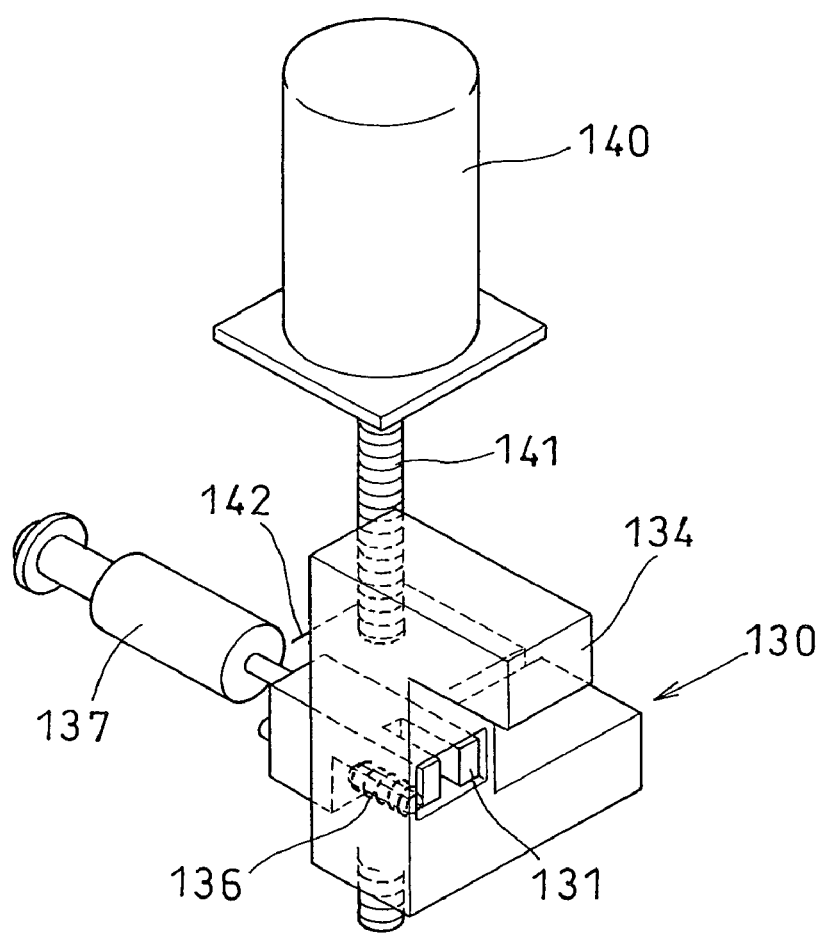
FIG. 6 is a concept view of the hook installed on the moving piece and its drive device.

FIG. 6 is a concept view of the hook installed on the moving piece and its drive device. The moving piece 130 has a horizontal section extending from the direct-driven actuator 142, a vertical section extending in parallel with the screw 141 from the horizontal section, and further has a press-contact piece 134 extending in a canopy (eaves) shape from the top side of the vertical section. The lower edge of the press-contact piece 134 for pressing the syringe, engages with the rear side of the plunger of the syringe 25. A through-hole is drilled horizontally in the vertical section, and a (tuning) fork type hook 131 protrudes below the press-contact piece 134 from this through-hole. The section (hook) for pulling in the syringe is applied with a force by a spring 136 to escape from below the press-contact piece 134, and is usually hidden within the moving piece. When the solenoid 137 positioned rearward of the hook 131 applies a force, the hook 131 compresses the spring 136 and protrudes below the press-contact piece 134 of the moving piece. To pull the plunger of the syringe 125 upward, the hook 131 is made to protrude below the press-contact piece 134 of the moving piece 130, and the narrow section of the plunger is enclosed by the (tuning) fork type hook 131 of press-contact piece 134. When the moving piece 130 moves upward while in this state, the hook 131 engages with the larger diameter of the plunger rear edge, and the plunger is pulled upward along with the rise of the hook 131. When the hook 131 is not required, the solenoid 137 is set to off, and the hook is stored within the moving piece with the spring 136 returning to the original position. In other words, the hook can move the plunger to a pull-in position or to non-pull storage position. To restate this from another perspective, the hook can change to a state that drives the plunger or to a state that does not drive the plunger.

The moving piece 130 contains a linear encoder as shown in FIG. 1, moving piece 130 position information is stored in the memory within the drive circuit 151 and can be monitored by a control computer 150. More specifically, a non-transparent film 143 formed as a straight line of slits is installed on a portion of the slider 142. When the slider 142 moves, it passes through the optical sensor 144 installed on the (device) main unit. The optical sensor 144 is made up of a light (photoelectric) sensor, and also of a light source consisting of a light emitting diode and a lens to form a parallel light beam. The optical sensor 144 is configured to optically count the number of slits passing between both (sensor and light source). A drive circuit 151 is able to recognize the amount of movement of moving piece 130 per unit of time by periodically checking the number of slits counted by the optical sensor 144, and the current position of the moving piece 130 can therefore be found from the total movement amount. An optical sensor 145 is installed to detect the highest position of the moving piece.

Figure 7:
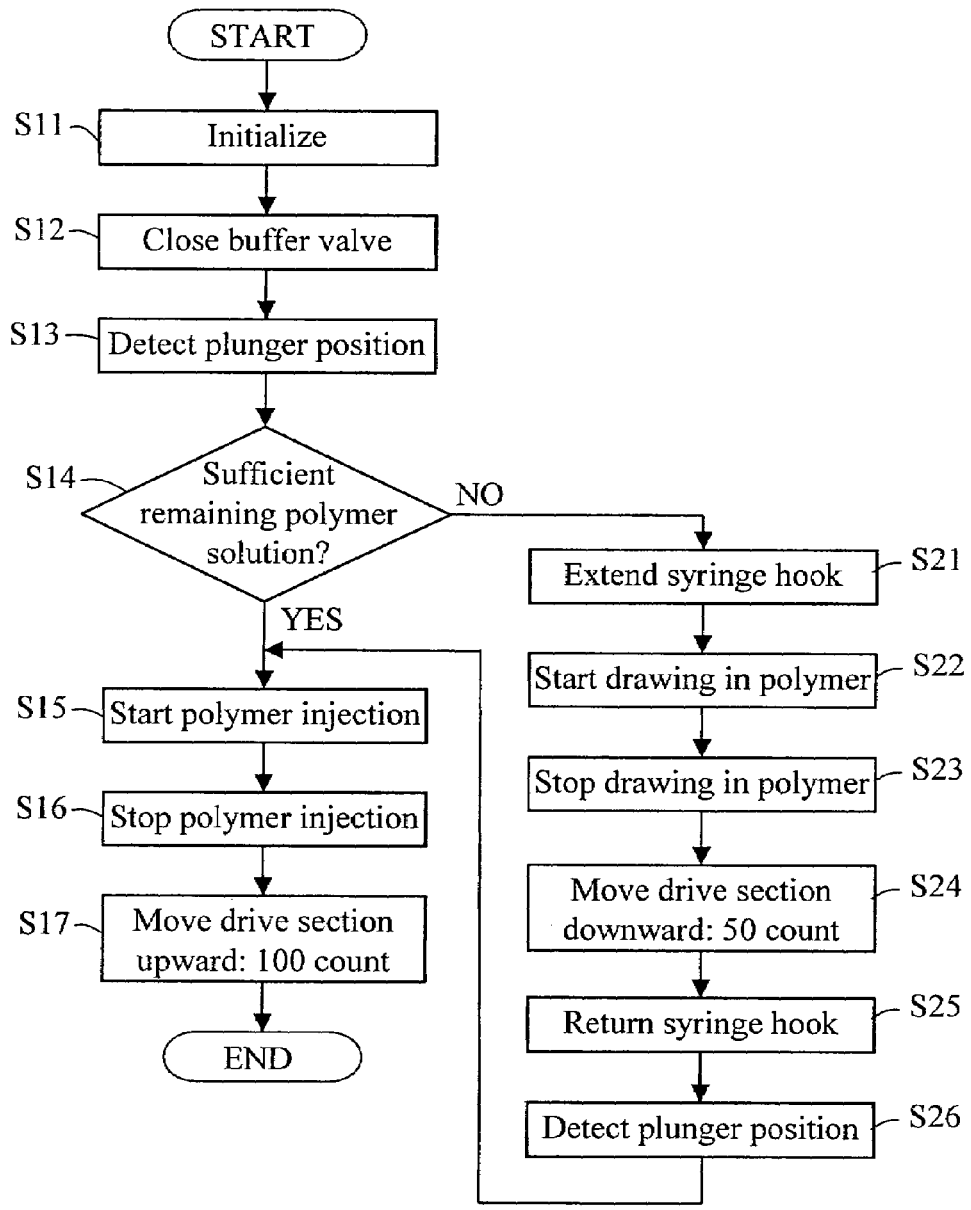
FIG. 7 is a flowchart showing the process of injecting the polymer solution into the capillary array.

The procedure for injecting the polymer solution into the capillary array is next described while referring to the flowchart in FIG. 7.

The drive section is initialized (reset) when the polymer injection command is issued (S11). The operation for initializing the drive section is the raising of the moving piece 130 to the highest position (position detected by optical sensor 145) and returning the encoder numerical value to zero (0) and then lowering the moving piece 130 and stopping at the position (encoder numerical value becomes 1 at this time) where the first slit was read out. This operation resets the numerical value of the encoder. This (initializing)

operation is necessary since the encoder numerical value will become zero (0) when the power is turned on, regardless of the position the moving piece is at. The encoder numerical value might also deviate during continued (cyclic) device operation so performing this (initializing) operation when first filling the polymer solution can prevent malfunctions (operating errors). In other words, by setting the moving piece 130 at the specified position when power is turned on or a polymer solution filling command is issued, (adverse) effects on the initial state of the glass syringe 125 can be prevented.

Next, the buffer valve 122 is closed (S12). The plunger position is then detected and the press-contact piece 134 of moving piece 130 is lowered to the syringe position (S13). The plunger position is detected by utilizing the characteristics of the stepping motor that stops rotating when the load becomes too large. When the moving piece 130 moves the plunger upward, that load itself becomes the main load so the slider of the actuator moves at a fixed speed. The moving piece 130 eventually makes contact with the plunger and when the plunger is pressed in at that point, a large load is applied to the actuator as the syringe internal pressure rises. As a result, the stepping motor stops rotating and the slider comes to a stop at that position. Therefore if the threshold is set to a speed lower than the usual speed of the slider, whether or not the moving piece 130 is making contact with the plunger can be determined. To detect the plunger position, the electrical current value of the motor is set to a low value in a range that will not hinder usual up/down operation, and so that the motor will quickly stop rotating when the moving piece 130 makes contact with the syringe. In actual operation, by checking the value of the linear encoder at periodic intervals, the moving piece can be determined to have made contact with the plunger at the point where the slide movement speed has become lower than the threshold value setting. The remaining amount of polymer solution within the glass syringe 125 can be checked (S14) from the encoder value at this time. Here, the "moving piece making contact with the plunger" does not signify direct contact but includes the meaning of indirect contact by way of a cushioning material to absorb direct impact between the moving piece and plunger. If the amount of compression of the shock-absorbing cushioning member varies each time it is impacted by the moving piece and plunger, the amount of remaining polymer solution cannot be correctly checked. Therefore, the amount of compression of the shock-absorbing cushioning member preferably is the same each time contact is made.

If the amount of remaining polymer solution within the glass syringe 125 is too low for the next polymer injection, the hook 131 is sent from the moving piece 130 (S21),the motor 140 rotates in reverse, the plunger of the glass syringe 125 is pulled up and polymer solution drawn (suctioned) out of the polymer bottle (S22) To prevent air bubbles from occurring at the connecting portion of the flow path due to a sudden drop in internal pressure and from the polymer solution itself, the rotation speed of the motor 14 is set to a speed matching the polymer viscosity and the plunger is pulled upward.

The higher the speed for suctioning the polymer solution into the syringe from the polymer storage container, the greater the device throughput that can be obtained. On the other hand, air bubbles occur in the flow path when the draw-in (suction) speed of the polymer solution is too fast. Air bubbles occur during electrophoresis cause effects that prevent correct analysis results from being obtained so that the occurrence of air bubbles must be prevented. To prevent this (air bubbles), a maximum allowable suction speed can be preset for each type of polymer solution and these (speed values) can be stored into the control computer 150. The throughput can then be improved by selecting a suction speed to match the type (viscosity) of polymer solution used during analysis. Once the suction speed is selected, the polymer solution can be automatically suctioned at that speed and analysis continuously performed.

The motor 140 stops (S23) after a check is made from the encoder value that sufficient polymer solution has been suctioned by the glass syringe 125. The moving piece 130 is then lowered slightly (S24), and after the hook 131 separates from the plunger, the hook 131 returns to the original position (S25). The stepping motor 140 then rotates in the forward direction and the moving piece is again lowered to the syringe position (S26).

The pressurization of the glass syringe 125 then starts, and the polymer solution is injected into the capillary of the capillary array unit 100 (S15). The electrical current flowing in the motor is regulated to a particular value so that the injection pressure does not exceed the pressure resistance of the syringe, and the output torque is adjusted. The encoder value is also periodically checked during polymer injection and the motor stops (S16) when determined from the differential versus the encoder value during start of injection that the specified amount of polymer solution was injected. The moving piece 130 is then raised and the pressure within the flow path released (S17) and injection of polymer solution ends. If an adequate amount of polymer solution can be confirmed to be available within the glass syringe 125 in the check of remaining polymer solution in step 14, then, polymer injection drive promptly starts in step 15.

The buffer valve 122 then opens, and the sample material is injected into the capillary array as shown in FIG. 5. The sample material injection tip of the capillary array unit 100 is next immersed in the buffer solution as shown in FIG. 1. A voltage is then applied so the sample material injection tip of the capillary array unit 100 becomes the negative electrode and the buffer container 121 side becomes the positive electrode and electrophoresis starts.

Figure 8:
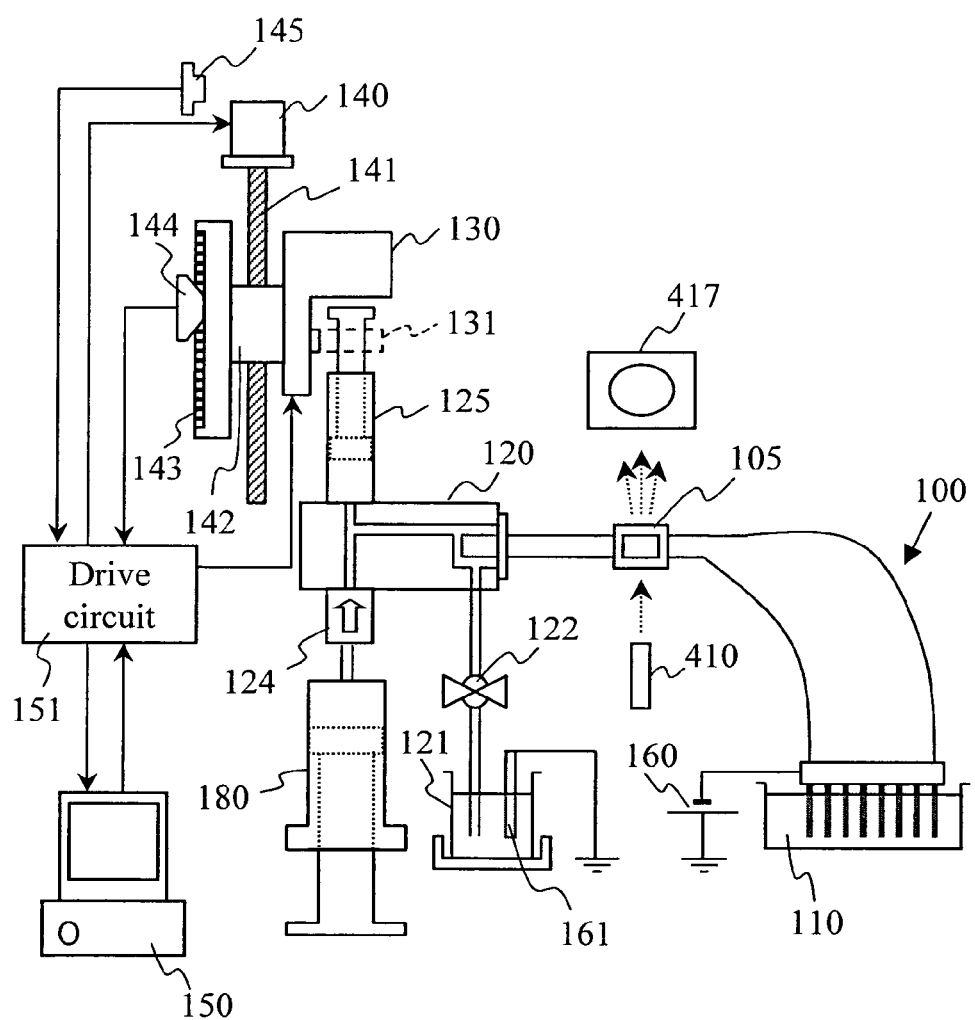
FIG. 8 is an overall structural view showing another example of the capillary electrophoresis device of the present invention.

FIG. 8 is an overall structural view showing another example of the capillary electrophoresis device of the present invention. The device of this example differs from the device shown in FIG. 1 in the point that the syringe 180 is utilized as the container for holding polymer solution for filling.

In the device shown in FIG. 1, the polymer bottle and buffer container are both open to the outer atmosphere during electrophoresis so that fluid will flow by itself from high level (fluid surface) to the low level (fluid surface) due to the high/low pressure differential. A check valve is therefore inserted between them (polymer bottle and buffer) to prevent fluid from flowing into the polymer bottle so that actually there is no flow of fluid from the buffer container to the polymer bottle. The liquid surface of the polymer bottle is therefore installed to be lower than the liquid surface of the buffer container to prevent fluid flow between them.

When the syringe 180 on the other hand, is used as the polymer bottle shown in FIG. 8, the frictional force of the syringe plunger is capable of preventing outflow of polymer solution from the syringe so that both containers can be installed in a desired location without having to worry about the positional relationship of the two containers.

INDUSTRIAL APPLICABILITY

The capillary electrophoresis device of the present invention having a polymer injection mechanism, automatically performs suctioning in of polymer from the polymer container and injection of polymer into the capillary array so that many measurements can be continuously performed and device throughput can be improved.

The invention claimed is:

1. A capillary electrophoresis device comprising:
a capillary array;
a polymer storage container for holding polymer solution;
a pressure-resistant syringe for pressurizing said polymer solution in said capillary array;
a buffer container for holding buffer solution;
a flow path block, to which a tip of said capillary array and said pressure-resistant syringe are connected, formed with flow paths for joining at least said tip of the capillary array, said polymer storage container, said pressure-resistant syringe, and said buffer container;
a check valve for allowing a fluid medium to flow towards said flow path block from said polymer storage container side and preventing said fluid medium from flowing from said flow path block towards said polymer storage container side; and
a plunger driver for driving said pressure-resistant syringe plunger in the push-in direction and pull-out direction;
further characterized by drawing polymer solution into said pressure-resistant syringe from said polymer storage container by way of said flow path block, and injecting said polymer solution drawn from said pressure-resistant syringe into said capillary array by way of said flow path block; and
characterized in that said plunger drive means has a stepping motor; a direct-driven actuator for converting the rotation of said stepping motor into linear movement; a moving piece for applying contact pressure to the rear edge of said plunger fixed to said direct-driven actuator; and a linear encoder for outputting a signal showing the position of said moving piece wherein said moving piece contains an inward/outward moving hook, and said plunger is clamped by said hook when said plunger is driven in the pull-out direction.

2. A capillary electrophoresis device according to claim 1, characterized in that said polymer storage container has a syringe structure.

3. A capillary electrophoresis device according to claim 1, characterized in that said polymer storage container and said buffer container are joined by said flow path, and are exposed to atmospheric air pressure, and the level of the polymer solution in said polymer storage container is lower than the level of said buffer solution in said buffer container.

4. A capillary electrophoresis device according to claim 1, characterized in that a plurality of speeds may be set as the plunger pull-out speed when drawing in said polymer solution to said syringe from said polymer storage container, and said plunger pull-out speed is selected according to the viscosity of said polymer solution.

5. A capillary electrophoresis device according to claim 1, characterized in that said flow path block has a side hole for insertion of said capillary array tip, and a flow path in said side hole at the upper edge of an end wall connects said pressure-resistant syringe and said polymer storage container, and a flow path on the bottom side of said side hole connects to said buffer container.

6. A capillary electrophoresis device comprising:
one or more capillaries capable of being filled with a separator medium for separating a sample;
a first buffer container for holding a first buffer solution for immersing a portion of said one or more capillaries;
a second buffer container for holding a second buffer solution;
polymer container for holding said separator medium;
a pressure-resistant syringe capable of drawing in and pushing out said separator medium;
a plunger shift mechanism having a press-force section to press the plunger of said pressure-resistant syringe, and a pull-in section to pull said plunger; said pull-in section being capable of changing from a state pulling the plunger to a state not pulling the plunger;
a first flow path joining said one or more capillaries and said second buffer container;
a second flow path joining said polymer container and said pressure-resistant syringe;
a third flow path joining said pressure-resistant syringe and said one or more capillaries; and
a check valve installed in said second flow path, allowing said separator medium to flow from said polymer container towards said pressure-resistant syringe, and for preventing said separator medium from flowing towards said polymer container from said pressure-resistant syringe.

7. A capillary electrophoresis device according to claim 6, characterized in that said plunger shift mechanism in the electrophoresis device is installed at the specified position by turning on the power to the electrophoresis device and/or by instructions to operate said pressure-resistant syringe.

8. A capillary electrophoresis device according to claim 6, characterized in that said plunger shift mechanism is shifted to the pull-in direction by turning on the power to the electrophoresis device and/or by instructions to operate said pressure-resistant syringe.

9. A method for drawing a separator medium into a pressure-resistant syringe capable of drawing in said separator medium and injecting said separator medium into one or more capillaries and having a shift mechanism capable of moving a plunger of said pressure-resistant syringe, comprising following steps being performed prior to injecting said separator medium into said one or more capillaries:
placing said shift mechanism in a specified position;
moving said shift mechanism to make contact with said plunger;
determining amount of said separator medium in said pressure-resistant syringe based on amount of movement of said shift mechanism from the specified position until making contact with said plunger; and
moving said shift mechanism to drive said plunger, and drawing in said separator medium into said pressure-resistant syringe when said separator medium within said pressure-resistant syringe is below a specified amount, wherein said shift mechanism has a pull-in section capable of raising said plunger, and moving said shift mechanism to drive said plunger comprises positioning the pull-in section capable of pulling up the plunger, to a plunger pull-up position.

10. A method for drawing a separator medium into a pressure-resistant syringe according to claim 9, further comprising the following step of:
moving the shift mechanism to drive said plunger, and injecting said separator medium into said one or more capillaries when said separator medium within said pressure-resistant syringe is a specified amount or more.

11. A method for drawing a separator medium into a pressure-resistant syringe capable of drawing in said separator medium and injecting said separator medium into one or more capillaries and having a shift mechanism capable of moving a plunger of said pressure-resistant syringe, comprising following steps being performed prior to injecting said separator medium into said one or more capillaries:

placing said shift mechanism in a specified position;

moving said shift mechanism to make contact with said plunger;

determining amount of said separator medium in said pressure-resistant syringe based on amount of movement of said shift mechanism from the specified position until making contact with said plunger; and moving said shift mechanism to drive said plunger at a movement speed based on the type of said separator medium, and drawing said separator medium into said pressure-resistant syringe when said separator medium within said pressure-resistant syringe is below a specified amount.

12. A method for drawing a separator medium into a pressure-resistant syringe according to claim 11, further comprising the following step of:

moving the shift mechanism to drive said plunger, and injecting said separator medium into said one or more capillaries when said separator medium within said pressure-resistant syringe is a specified amount or more.

* * * * *

UNITED STATES PATENT AND TRADEMARK OFFICE
CERTIFICATE OF CORRECTION

PATENT NO. : 7,081,191 B2
APPLICATION NO. : 10/239308
DATED : July 25, 2006
INVENTOR(S) : Tomohiro Shoji et al.

It is certified that error appears in the above-identified patent and that said Letters Patent is hereby corrected as shown below:

Title page Item (75), Inventors: correct the name of the first inventor, "Tomihiro Shoji," to read -- Tomohiro Shoji --.

Signed and Sealed this

Twenty-seventh Day of February, 2007

JON W. DUDAS
*Director of the United States Patent and Trademark Office*